(12) United States Patent
Studenec et al.

(10) Patent No.: US 11,925,360 B2
(45) Date of Patent: Mar. 12, 2024

(54) METHOD FOR PREVENTING KINKED TUBING IN AN ARTHROSCOPIC IRRIGATION PUMP

(71) Applicant: Conmed Corporation, Utica, NY (US)

(72) Inventors: Mark S. Studenec, Kenneth City, FL (US); James J. Alberti, Odessa, FL (US); Eric N. Stubkjaer, Gulfport, FL (US)

(73) Assignee: Conmed Corporation, Utica, NY (US)

( * ) Notice: Subject to any disclaimer, the term of this patent is extended or adjusted under 35 U.S.C. 154(b) by 57 days.

(21) Appl. No.: 16/672,751

(22) Filed: Nov. 4, 2019

(65) Prior Publication Data

US 2020/0139042 A1   May 7, 2020

Related U.S. Application Data

(60) Provisional application No. 62/754,838, filed on Nov. 2, 2018.

(51) Int. Cl.
```
A61B 17/16    (2006.01)
A61M 1/00     (2006.01)
A61M 3/02     (2006.01)
```
(52) U.S. Cl.
CPC ...... *A61B 17/1622* (2013.01); *A61B 17/1659* (2013.01); *A61M 1/74* (2021.05);
(Continued)

(58) Field of Classification Search
CPC ........ A61B 2217/007; A61B 2218/002; A61B 2017/00199; A61B 34/25; G06F 1/1613; G06F 1/166; H01M 2/10; H04M 1/0202; H05K 5/0234; H05K 5/0204; F16M 2200/08; F16M 11/041; F16M 11/24; F16M 11/36; F17C 2205/018; A47B 91/00; A47B 2220/0027; A47B 13/021; A47B 91/005; A47B 91/02; A47B 91/024; A47B 23/042; A47B 2097/008; A47B 91/022;
(Continued)

(56) References Cited

U.S. PATENT DOCUMENTS

| 938,883 A | * | 11/1909 | Maier | A47B 91/04 |
| | | | | 190/18 R |
| 1,726,121 A | * | 8/1929 | Polkosnik | A47B 91/04 |
| | | | | 248/188.9 |

(Continued)

*Primary Examiner* — Scott J Medway
(74) *Attorney, Agent, or Firm* — Bond, Schoeneck & King, PLLC; Frederick J. M. Price

(57) ABSTRACT

An irrigation system having attachable anti-sliding features that prevent movement of the system along a surface. The irrigation system includes a console having a front panel with an inflow pump and an outflow pump. The front panel extends to a front edge of the console and the front edge is connected to a bottom side of the console. The attachable anti-sliding features include one or more feet attached to the bottom side of the console. Each foot has an L-shaped body having a first end and a second end with a first surface and an opposing second surface both extending between the first end and the second end. A protrusion extends from the second end of the body, forming the L-shape. The one or more feet are attached to the bottom side of the console such that the protrusion extends away from the console.

8 Claims, 10 Drawing Sheets

(52) U.S. Cl.
CPC ............... *A61M 1/77* (2021.05); *A61M 1/83* (2021.05); *A61M 3/0216* (2014.02); *A61M 3/022* (2014.02); *A61M 3/0258* (2013.01); *A61M 3/0279* (2013.01); *A61B 2217/005* (2013.01); *A61B 2217/007* (2013.01); *A61M 3/0202* (2021.05); *A61M 2205/50* (2013.01); *A61M 2205/6081* (2013.01)

(58) Field of Classification Search
CPC .. A47B 91/026; A47B 91/028; A61M 3/0258; A61M 2205/12; A61M 2205/3344; A61M 2205/50; A61M 3/0216
USPC ...... 248/284.1, 188.8, 188.9, 677, 501, 615, 248/188.4; 211/119.005; 312/531.1
See application file for complete search history.

(56) References Cited

U.S. PATENT DOCUMENTS

| | | | | |
|---|---|---|---|---|
| 1,786,458 A * | 12/1930 | Shipman | | A47C 9/02 182/46 |
| 2,088,566 A * | 8/1937 | Allen | | F16F 3/093 248/615 |
| 2,849,201 A * | 8/1958 | Schelgunov | | A47B 91/00 24/619 |
| 2,973,233 A * | 2/1961 | McPhee | | F16B 9/052 248/188 |
| 3,092,364 A * | 6/1963 | Sarafinas | | H04M 1/02 248/687 |
| 3,103,332 A * | 9/1963 | Waters | | A47B 91/06 248/615 |
| 3,337,167 A * | 8/1967 | Johnson | | F16F 1/371 248/615 |
| 3,518,728 A * | 7/1970 | Phillips | | A47B 97/00 24/287 |
| 3,565,377 A * | 2/1971 | Schreyer | | A47B 17/003 248/188.4 |
| 3,778,125 A * | 12/1973 | Gutmann, Jr. | | A47B 21/00 312/196 |
| 3,814,363 A * | 6/1974 | Brelosky | | A47L 15/4253 248/188.4 |
| 4,192,601 A * | 3/1980 | Frankel | | F16M 11/10 248/441.1 |
| 4,313,112 A * | 1/1982 | Foster | | A47B 21/00 108/92 |
| 4,349,173 A * | 9/1982 | Volka | | A47B 37/02 248/346.06 |
| 4,368,867 A * | 1/1983 | Pendleton | | F16M 11/10 248/346.06 |
| 4,394,563 A * | 7/1983 | Schnell | | F16M 11/22 219/520 |
| 4,396,177 A * | 8/1983 | Liebl | | F16M 11/22 248/188.9 |
| 4,511,111 A * | 4/1985 | Godfrey | | A47B 21/0314 248/346.5 |
| 4,549,767 A * | 10/1985 | Hampshire | | A47B 19/06 297/423.46 |
| 4,696,089 A * | 9/1987 | Gjesdal | | B25B 27/28 29/451 |
| 4,767,105 A * | 8/1988 | Caspers | | G11B 33/02 267/140 |
| 4,846,435 A * | 7/1989 | Cohen | | A47B 81/06 248/346.01 |
| D308,773 S * | 6/1990 | Morrow | | D6/406.4 |
| RE33,556 E * | 3/1991 | Berke | | A47B 21/0371 211/69.1 |
| 5,020,768 A * | 6/1991 | Hardt | | F16M 11/22 248/188 |
| 5,040,760 A * | 8/1991 | Singer | | A47B 21/0314 248/172 |
| 5,040,766 A * | 8/1991 | Egly | | B41J 11/58 248/676 |
| D338,882 S * | 8/1993 | Reiter | | D14/447 |
| 5,261,648 A * | 11/1993 | Kardos | | F16F 15/08 248/638 |
| 5,277,554 A * | 1/1994 | Elson | | F04B 39/00 417/363 |
| 5,388,792 A * | 2/1995 | Hastings | | F16M 11/22 248/188.1 |
| 5,400,998 A * | 3/1995 | Ma | | H05K 5/0234 248/677 |
| D358,381 S * | 5/1995 | Merino | | D14/451 |
| 5,431,365 A * | 7/1995 | Hopkins | | A44B 11/223 24/170 |
| 5,511,758 A * | 4/1996 | Hsu | | F16M 13/00 248/461 |
| 5,517,354 A * | 5/1996 | Mika | | G02B 21/24 359/394 |
| 5,690,303 A * | 11/1997 | Winters | | A47B 91/00 248/188.3 |
| 5,868,372 A * | 2/1999 | Novak | | A47B 91/00 248/346.11 |
| 5,887,962 A * | 3/1999 | Tsai | | F16M 11/22 312/351.9 |
| 6,098,952 A * | 8/2000 | Tonn | | F16M 11/10 248/688 |
| 6,193,208 B1 * | 2/2001 | Schmitt | | F16M 11/22 248/188 |
| 6,209,465 B1 * | 4/2001 | Brooks | | A47B 91/02 108/150 |
| 6,302,543 B1 * | 10/2001 | Arai | | H04N 9/3141 348/E5.143 |
| 6,311,941 B1 * | 11/2001 | Feldmeyer | | A47B 97/00 248/188.8 |
| 6,357,717 B1 * | 3/2002 | Kennard, IV | | F16F 15/08 248/633 |
| 6,669,164 B1 * | 12/2003 | Bohman | | A47B 21/0314 248/393 |
| 6,690,512 B2 * | 2/2004 | Konopa | | G02B 21/24 359/368 |
| 6,707,668 B2 * | 3/2004 | Huang | | G06F 1/203 248/676 |
| 6,745,986 B1 * | 6/2004 | Bright | | A47B 21/0314 108/50.01 |
| 6,814,416 B2 * | 11/2004 | Helot | | F16M 11/24 248/677 |
| D519,121 S * | 4/2006 | Zamanian | | D14/447 |
| 7,095,610 B1 * | 8/2006 | Banko | | G06F 1/1616 248/615 |
| 7,442,161 B2 * | 10/2008 | Gainer | | G03B 23/00 353/70 |
| 7,450,371 B2 * | 11/2008 | Searby | | F16M 11/041 361/679.55 |
| 7,550,668 B2 * | 6/2009 | Chen | | H05K 5/0234 174/50 |
| 7,600,730 B2 * | 10/2009 | Leung | | F16M 11/26 248/676 |
| 7,663,876 B2 * | 2/2010 | Lin | | G06F 1/203 361/679.47 |
| 7,690,617 B2 * | 4/2010 | Takao | | F16M 13/02 248/499 |
| 7,733,645 B2 * | 6/2010 | Hsu | | H05K 5/02 361/679.59 |
| 8,139,357 B2 * | 3/2012 | Trang | | G06F 1/203 400/681 |
| 8,305,753 B2 * | 11/2012 | Chang | | G06F 1/166 361/679.59 |
| 8,334,936 B2 * | 12/2012 | Takao | | F16M 11/42 348/836 |
| 8,491,067 B2 * | 7/2013 | Chen | | H05K 5/0234 312/223.2 |
| 8,491,129 B2 * | 7/2013 | Koyama | | G03B 21/145 353/70 |
| 8,579,393 B2 * | 11/2013 | Song | | G06F 1/181 312/351.9 |
| 8,584,916 B1 * | 11/2013 | Chen | | A45F 5/021 224/199 |

(56) References Cited

U.S. PATENT DOCUMENTS

| | | | | | |
|---|---|---|---|---|---|
| 8,794,579 | B2* | 8/2014 | Sturman | ............ | F16M 11/2092 248/284.1 |
| 8,876,071 | B2* | 11/2014 | Brooke | ................. | A47B 91/16 248/188.8 |
| 8,915,558 | B2* | 12/2014 | Sween | ................... | A47B 21/04 312/223.3 |
| 9,375,078 | B2* | 6/2016 | Doerflinger | ............ | A47B 31/00 |
| 9,685,984 | B1* | 6/2017 | Majumdar | ............ | G06F 1/1616 |
| 9,885,377 | B2* | 2/2018 | Ku | ........................ | F16B 12/44 |
| 10,306,177 | B2* | 5/2019 | Tanaka | ..................... | H04N 5/64 |
| 10,533,753 | B2* | 1/2020 | Lando | ................... | F24C 15/107 |
| 10,663,175 | B2* | 5/2020 | Jang | ..................... | F24C 15/086 |
| 2002/0140909 | A1* | 10/2002 | Tanaka | .................. | F16M 11/10 353/70 |
| 2003/0076018 | A1* | 4/2003 | Helot | ..................... | F16M 11/24 312/223.2 |
| 2003/0231466 | A1* | 12/2003 | Huang | ................... | G06F 1/203 361/679.48 |
| 2005/0015928 | A1* | 1/2005 | Arsenault | ........... | B60B 33/0049 16/300 |
| 2005/0029415 | A1* | 2/2005 | Ma | ........................ | F16M 13/00 248/166 |
| 2005/0116134 | A1* | 6/2005 | Lee | ..................... | D06F 39/125 248/650 |
| 2005/0121583 | A1* | 6/2005 | Cavello | ................. | A47B 49/00 248/349.1 |
| 2006/0043252 | A1* | 3/2006 | Lee | ..................... | G03B 21/145 353/70 |
| 2006/0198092 | A1* | 9/2006 | Searby | ................. | F16M 11/041 361/679.02 |
| 2007/0177342 | A1* | 8/2007 | Mundt | ................. | G06F 1/1613 361/679.55 |
| 2007/0286410 | A1* | 12/2007 | Daly | ..................... | F16M 11/10 379/436 |
| 2007/0290104 | A1* | 12/2007 | Denison | ................ | F16M 11/36 248/188.8 |
| 2008/0154095 | A1* | 6/2008 | Stubkjaer | ............ | A61M 3/0258 600/156 |
| 2008/0154182 | A1* | 6/2008 | Martin | ................ | A61M 1/0072 604/27 |
| 2008/0154184 | A1* | 6/2008 | Blight | ................. | A61M 3/0216 604/30 |
| 2008/0154185 | A1* | 6/2008 | Blight | ................. | A61M 3/0258 604/31 |
| 2008/0253081 | A1* | 10/2008 | Tracy | ..................... | G06F 1/203 361/679.5 |
| 2009/0043252 | A1* | 2/2009 | Haylor | ................ | H05K 5/0234 604/67 |
| 2009/0175001 | A1* | 7/2009 | Mathew | ................ | H05K 5/0234 248/688 |
| 2011/0069446 | A1* | 3/2011 | Trang | ..................... | G06F 1/1632 361/679.55 |
| 2011/0228176 | A1* | 9/2011 | Takao | .................... | F16M 11/42 348/836 |
| 2012/0212886 | A1* | 8/2012 | Chou | .................... | F16M 11/2014 361/679.01 |
| 2013/0075550 | A1* | 3/2013 | Chiu | ..................... | G06F 1/1656 248/188.9 |
| 2013/0301193 | A1* | 11/2013 | Abe | ..................... | H05K 5/0234 361/679.5 |
| 2014/0139082 | A1* | 5/2014 | Green | ..................... | F16M 11/048 248/125.3 |
| 2016/0029784 | A1* | 2/2016 | Pike | ..................... | A47B 9/10 248/188.2 |
| 2016/0100693 | A1* | 4/2016 | Urban | ..................... | A47D 7/00 5/8 |
| 2016/0252207 | A1* | 9/2016 | Hollenberg | ............ | G01D 11/30 73/866.5 |
| 2017/0037994 | A1* | 2/2017 | Sakaguchi | ........... | F16M 11/045 |
| 2017/0074719 | A1* | 3/2017 | Izumo | ................. | A47B 91/024 |
| 2017/0311719 | A1* | 11/2017 | Vandenham | ........... | A47B 96/06 |
| 2018/0275723 | A1* | 9/2018 | Wang | ........................ | G06F 1/16 |
| 2019/0365483 | A1* | 12/2019 | Canady | ................ | A61M 13/003 |
| 2020/0319670 | A1* | 10/2020 | Elsey | .................... | G06F 1/1681 |
| 2020/0342976 | A1* | 10/2020 | Canady | ................ | A61B 18/1233 |

* cited by examiner

METHOD FOR PREVENTING KINKED TUBING IN AN ARTHROSCOPIC IRRIGATION PUMP

CROSS-REFERENCE TO RELATED APPLICATION

The present application claims priority to and the benefit of U.S. Provisional Patent Application No. 62/754,838, filed on Nov. 2, 2018 and entitled "Method for Preventing Kinked Tubing in an Arthroscopic Irrigation Pump," the entirety of which is incorporated herein by reference.

BACKGROUND OF THE INVENTION

1. Field of the Invention

The present invention relates to a surgical system and, more particularly, to an anti-sliding feature attachable to an irrigation system that prevents movement of the system along a surface.

2. Description of Related Art

Minimally invasive surgery, also referred to herein as endoscopic surgery, often utilizes an irrigation system to force suitable biocompatible fluid into the area surrounding the surgical work site within a patient. The term "irrigation" is used broadly to mean any type of pressurized fluid flow whether it be for irrigation in particular or for other uses described below. Flexible plastic tubing is used to conduct the fluid from a source to the work site and from the work site to a drain or other receptacle. Flexible tubing is also sometimes used as a pressure monitoring line to convey fluid pressure information to a control mechanism. Depending upon the procedure, the irrigating fluid is useful for various purposes such as tissue lavage, hydro-dissection, joint distension, uterine distension, etc. Known irrigation systems include electrically driven pump systems, in which a suitable fluid is pumped through flexible tubes from a source to the work site, gravity-feed systems, in which the pump is replaced by merely adjusting the height of the fluid supply above the patient, and nitrogen powered systems.

Current irrigation consoles either have no means of preventing them from sliding backward on a shelf or counter top, or must use mounting features (holes) on the console chassis which interface with pins mounted to shelves on a medical cart. An irrigation console sliding back (inward) on a shelf surface or counter top can cause multiple issues. Such issues include difficulty interfacing with console controls and the creation of a kink in the tubing set by the shelfs front edge. Kinked tubing can cause occlusion, limiting both inflow and outflow of saline solution to the joint, causing a delay in surgery.

Console mounting features are often located in the back on the device, which makes accessing the locking fasteners difficult in the limited area of the cart shelf space. As a result, users often do not apply the fasteners, thereby defeating the purpose of the mounting feature (i.e., to ease relocation and/or maintenance of the console). Also, if the console is placed on a surface not designed with the mating feature (such as a counter-top or an alternative manufacturer's cart), nothing prevents the console from sliding back and potentially causing aforementioned issues.

Therefore, there is a need for an anti-sliding feature for preventing movement of an irrigation system along a surface.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to an irrigation system having attachable anti-sliding features that prevent movement of the system along a surface. According to an aspect, the irrigation system includes a console having a front panel with an inflow pump and an outflow pump. The front panel extends to a front edge of the console and the front edge is connected to a bottom side of the console. The attachable anti-sliding features include one or more feet attached to the bottom side of the console. Each foot has an L-shaped body having a first end and a second end with a first surface and an opposing second surface both extending between the first end and the second end. A protrusion extends from the second end of the body, forming the L-shape. The one or more feet are attached to the bottom side of the console such that the protrusion extends away from the console.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
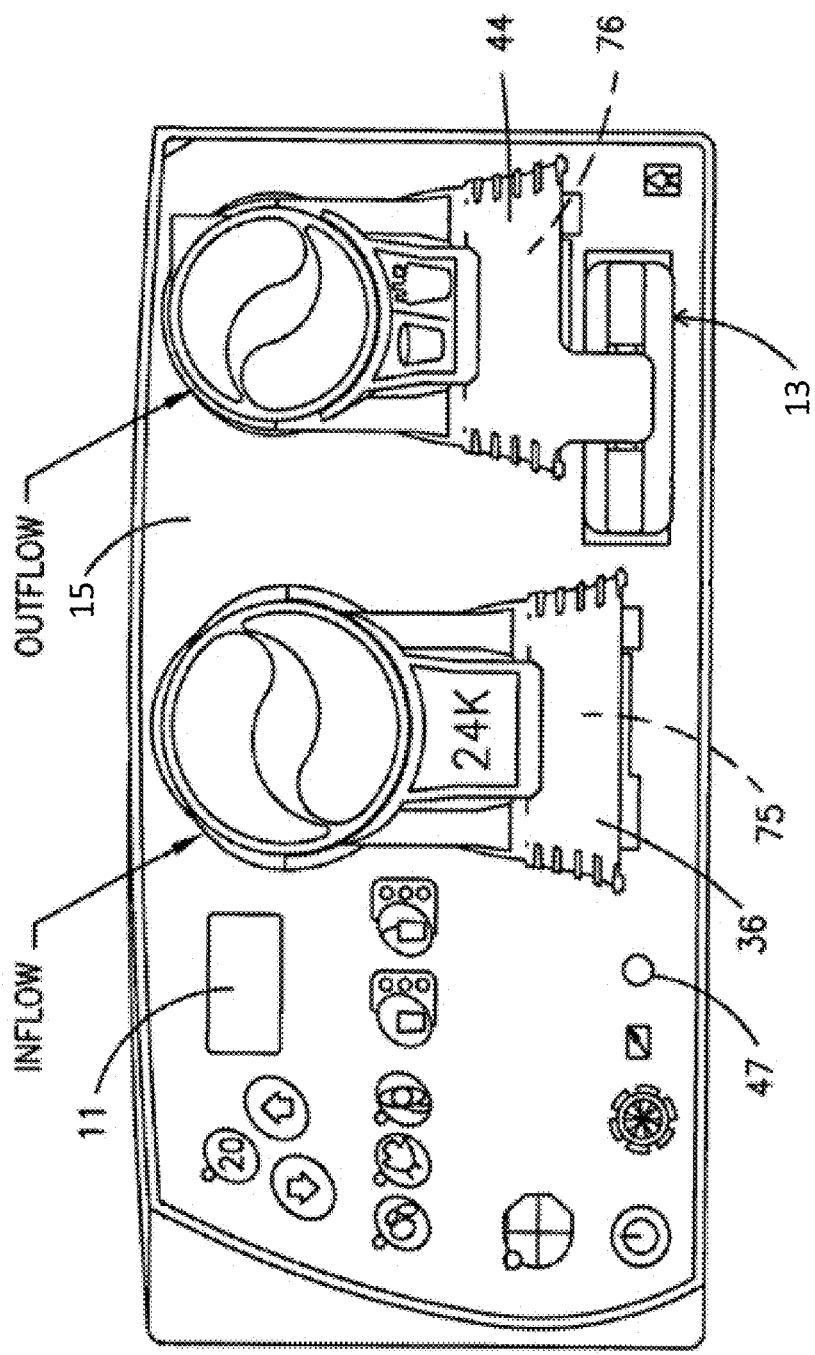
FIG. 1 is a front elevation view of a dual pump irrigation/aspiration console, according to an embodiment.
Figure 2:
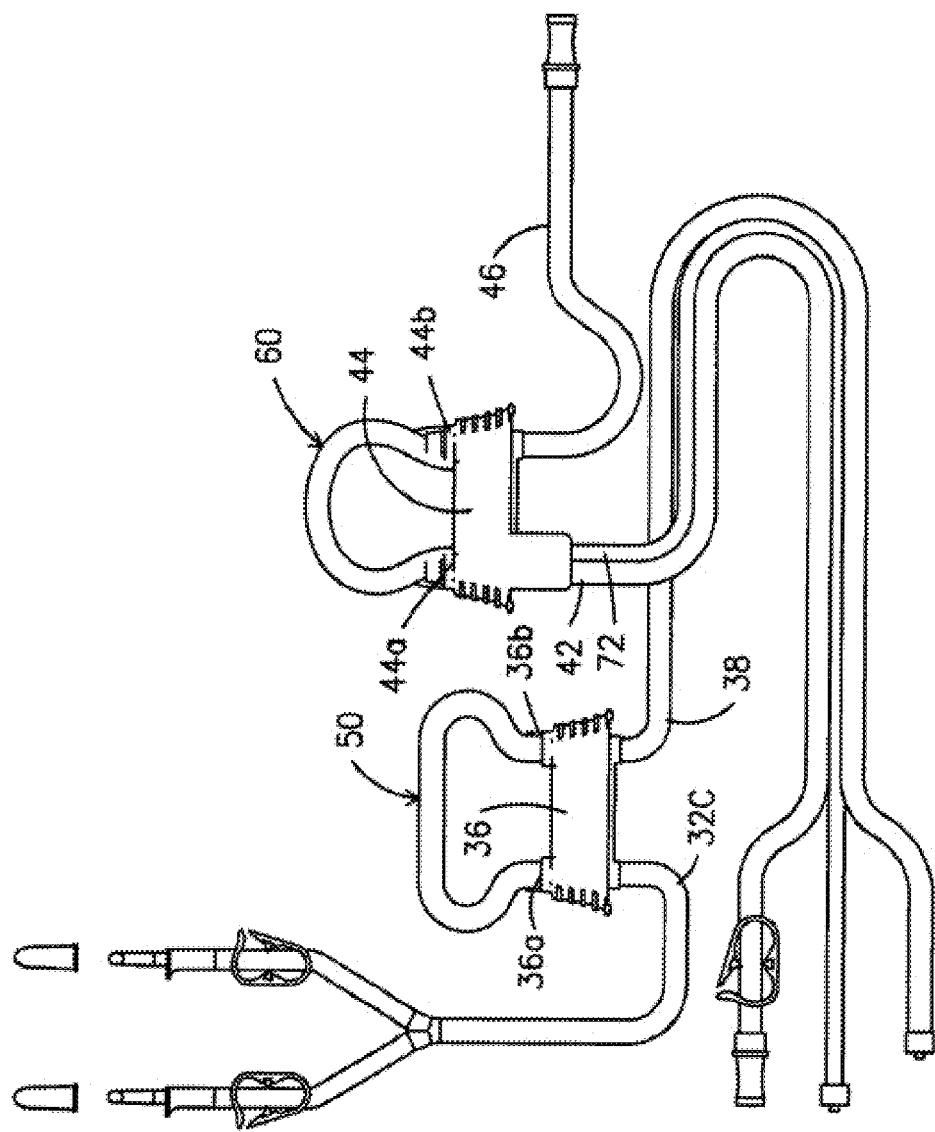
FIG. 2 is a schematic view of the tubing set for use with the console of FIG. 1, according to an embodiment.
Figure 3:
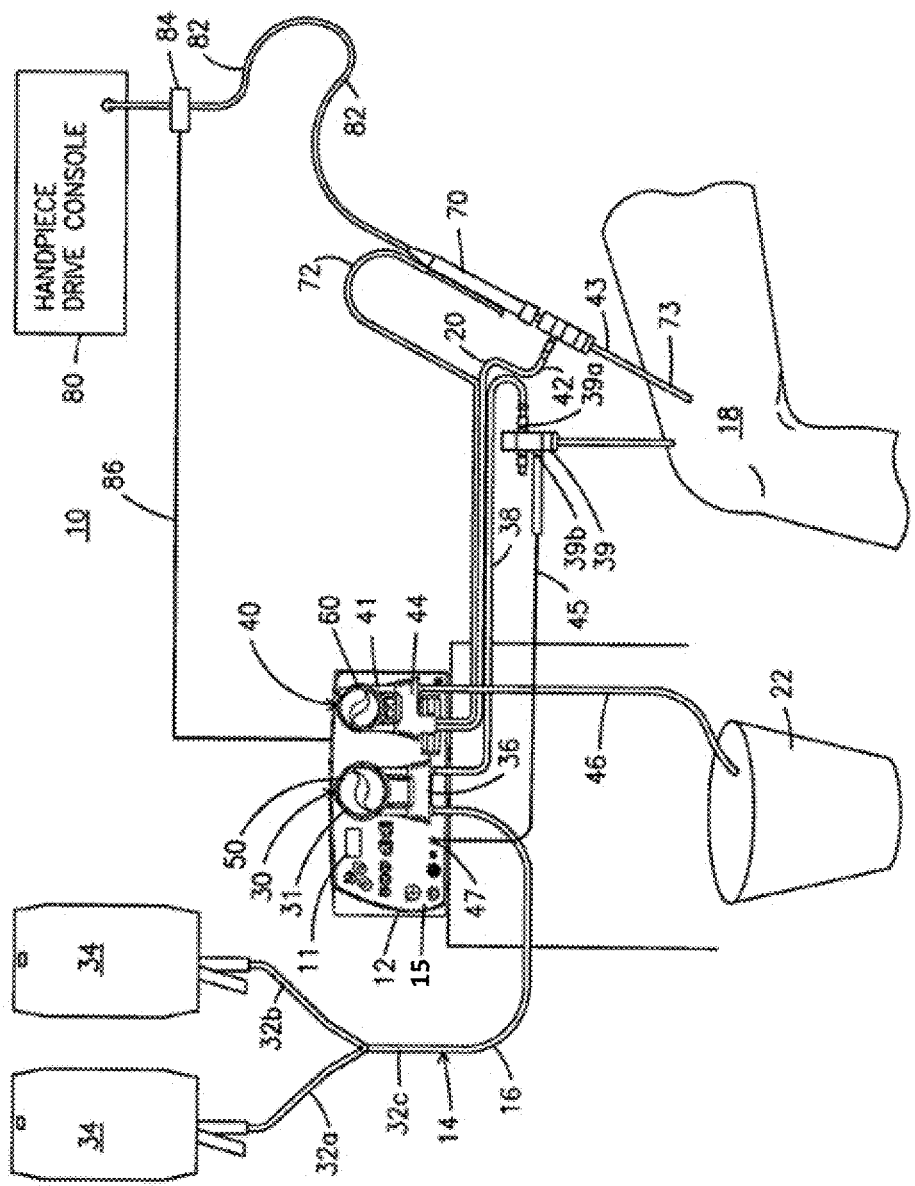
FIG. 3 is a view of the console of FIG. 1 assembled with the tubing set of FIG. 2 for use during an arthroscopic procedure, according to an embodiment.

Referring now to the drawings, wherein like reference numerals refer to like parts throughout, there is seen in FIGS. 1-3, an exemplary dual pump irrigation/aspiration system 10 constructed in accordance with the principles of this invention and comprising pump console 12 and tubing set 14. One such pump system 10 is disclosed in U.S. Pat. No. 7,510,542 assigned to the assignee hereof and incorporated by reference herein in its entirety. The pump system 10 is adapted to deliver irrigating fluid from a fluid source to a surgical work site, at a selected pressure and flow rate.

An exemplary set up of the pump system 10 at a surgical work site is shown in FIG. 3. The pump system 10 is suitable for use during a variety of selected surgical procedures and is, therefore, designed to be operable over a wide range of pressure and flow as selected by the user on a control panel display 11 by up/down pressure control buttons to set desired pressure and up/down flow rate control buttons to set desired flow. After being set, the control panel display 11 can show actual pressure and/or flow. In a preferred embodiment, the pressure is selectable in 5 mm Hg increments between approximately 0 and 150 mm Hg. The inflow flow rate is selectable between approximately 0 and 2,500 ml/min (milliliters/minute) in the laparoscopic mode and in discrete amounts of 50, 100 or 150 ml/min in the arthroscopic mode (with the outflow flow rate also being 50, 100 or 150 ml/min respectively). As disclosed and explained in U.S. Pat. No. 7,510,542, the rates may increase when auxiliary devices are used to remove a greater amount of fluid. Pressure and flow rate are both controlled by a flow control system incorporated into the system 10, the flow control system being microprocessor controlled and menu-driven. The pump console 12 and tubing set 14 serve to communicate fluid from a source 34 via an irrigation or inflow tubing 16 to the work site 18 and from the work site 18 via an aspiration or outflow tubing 20 to a drain 22. The pump console 12 comprises an inflow peristaltic pump 30 and an outflow peristaltic pump 40.

The tubing set 14 comprises a plurality of elongated flexible conduits (such as polyvinyl chloride (PVC) tubes) which are retained in predetermined relationships to each other by cassettes 36 and 44 situated at points intermediate the ends of the various tubes of the tubing set. The tubing cassettes 36 and 44 facilitate the engagement of the tubing set 14 to the console 12 by holding intermediate peristaltic roller tubes 50 and 60, respectively, in predetermined open loop shapes (where the ends of the tubes 50, 60 are attached to laterally spaced bores on the cassette housings), as shown in FIG. 2. This enables the user to easily and one-handedly place the two cassettes into position at their respective cassette receiving stations on pump console 12.

The tubing set 14 is representative of a disposable tubing set usable with the pump system 10. Each tubing set 14 may be associated with a particular procedure and may have a differently colored cassettes or cassette labels and each separate tube attached to each cassette could be identified by different colors or markings to facilitate hooking up the system to the patient and fluid supplies. The different colors or other indicia could indicate that the code associated with the tubing set causes the system to be programmed to automatically limit flow and pressure ranges depending upon the procedure for which the tubing set is designed.

Tubing set 14 comprises inflow tubing 16 and outflow tubing 20. Inflow tubing 16 comprises inflow tubes 32*a*, 32*b* and 32*c*, inflow cassette 36 and inflow tube 38. Tubes 32*a*, 32*b* and 32*c* provide for communicating fluid from fluid source(s) 34 to inflow tubing cassette 36 attached to the inflow peristaltic pump 30 and then to inflow tube 38 connected to an endoscope sheath 39 or other appropriate inflow device to communicate the fluid to the work site 18. Outflow tubing 20 comprises a main outflow tube 42, outflow cassette 44, auxiliary outflow tube 72 and outflow tube 46. Outflow tube 42 is connected to a working cannula 43 and is adapted to provide a normal, relatively low flow fluid outflow path for fluid being aspirated from the work site 18. Auxiliary outflow tube 72 is adapted to provide increased fluid outflow from the work site 18. Both outflow tubes 42 and 72 are connected to the outflow peristaltic pump 40.

Inflow tubing 16 further comprises the aforementioned intermediate roller tube 50 (on inflow cassette 36) interposed between inflow tubes 32*a* and 38. Cassette 36 and roller tube 50 are adapted to engage inflow peristaltic pump 30 at an inflow cassette receiving station 31 on the front of pump console 12. Outflow tubing 20 further comprises outflow cassette 44 which is adapted to hold the aforementioned intermediate roller tube 60 interposed between outflow tubes 42/72 and 46. Outflow cassette 44 and outflow intermediate roller tube 60 are adapted to engage outflow peristaltic pump 40 at an outflow cassette receiving station 41. Each cassette 36 and 44 is provided with a pressure transducer member on its rear surface. Both cassette receiving stations 31 and 41 have pressure sensors 75 and 76, respectively, on front panel 15 behind cassettes 36 and 44, respectively, as best seen in FIG. 1. The sensors 75 and 76 are adapted to read the pressure when the associated cassette is properly installed.

The operation and structure of cassettes 36 and 44 and pressure sensors 75 and 76 is best understood by reference to U.S. Design Patent 513,801 (Stubkjaer) issued Jan. 24, 2006. U.S. Design 513,320 (Stubkjaer) issued Dec. 27, 2005 and U.S. Pat. No. 7,273,359 (Blight et al.) issued Sep. 25, 2007, all assigned to the assignee hereof and incorporated by reference herein.

Cassettes 36 and 44 facilitate the attachment of tubing set 14 to the input and output peristaltic pumps 30 and 40, respectively. In a preferred embodiment, the cassettes are further improved by making the sizes of certain components on the inflow side of the system different from the sizes on the outflow side to avoid improper installation of tubing set 14 on pump console 12. Attachment of the tubing improperly could create an unsafe situation. While size variations may be achieved in a variety of ways, in the preferred embodiment as best seen in FIGS. 1-3 the size of the loop formed by inflow intermediate roller tube 50 is different than the size of the loop formed by the outflow intermediate roller tube 60. The relative sizes of the roller assembly of each peristaltic pump are also different and adapted to fit on and work with the chosen loop size. The size of the inflow and outflow cassettes and the tube lengths, i.e. the distances along the intermediate roller tubes between the loop ends 36a and 36b, and 44a and 44b, respectively (i.e. the length of the roller tubes), is varied to assure that cassettes 36 and 44 can only be installed one way on their respective receiving station.

Still referring to FIG. 3, during a surgical procedure, a shaver blade handpiece 70 may be used within cannula 43 in conjunction with a shaver blade 73 to resect tissue and otherwise remove debris from the work site 18. The resected tissue and debris are aspirated from the work site 18 along with fluid via cannula 43 and main outflow tube 42. This fluid path is normally open and the fluid flows at a relatively low rate during the surgical procedure to maintain pressure at the site and to clear debris. However, when handpiece 70 is operating, fluid is made to flow at a higher rate via auxiliary outflow tube 72. In a preferred embodiment, system 10 further comprises a means to identify when shaver handpiece 70 is operating so that the pump control system can automatically establish the higher rate of flow. This is accomplished by sensing a predetermined operating parameter of the handpiece 70 and using this information to activate a fluid diverter.

As shown in FIG. 3, to use a shaver handpiece 70, a handpiece drive console 80 is connected via power line 82 to handpiece 70. In a preferred embodiment, a shaver sensor means 84 is used to sense operation of the handpiece by detecting a parameter associated with the power line 82 attached to the handpiece 70. Sensor 84 is connected via signal line 86 to pump console 12. Sensor 84 via associated circuitry in pump console 12 identifies when the handpiece 70 is activated and therefore when the fluid flow rate through inflow cassette 36 and outflow cassette 44 must increase to compensate for the fluid withdrawn from the work site by handpiece 70.

To achieve a high flow mode, in addition to increasing the flow rate through inflow cassette 36, the control signal from shaver sensor 84 is used to activate a fluid diverter in the form of a shuttle valve 13, as shown in FIG. 1. Shuttle valve 13 is placed on the front panel 15 adjacent outflow cassette 44 at the point near where outflow tubes 42 and 72 enter a manifold (not shown) on outflow cassette 44. The manifold is an element having two fluid inputs and one common output which serves to join both tubes 42 and 72 to a common peristaltic outflow intermediate roller tube 60. The flow to the input side of intermediate roller tube 60 is controlled by passing both of the two fluid input tubes (i.e. outflow tubes 42 and 72) through shuttle valve 13. Shuttle valve 13 is a pinch valve that operates by alternatingly pinching one or the other of the outflow tubes 42 or 72 closed. Shuttle valve 13 is accessible on the front panel 15 of pump housing 12 adjacent the outflow peristaltic pump 40.

Pump system 10 utilizes a pressure sensing system to control the operation of inflow and outflow peristaltic pumps 30 and 40. System 10 monitors the pressure at the surgical site and increases or decreases fluid flow through tubing set 14 to maintain the surgeon requested pressure (i.e. set pressure) at the site while maintaining some outflow to clear debris, etc. from the site. The system 10 uses sensed and/or calculated/inferred pressure information to adjust various parameters to maintain set pressure. The pump fluid control system can operate by receiving pressure information from either the inflow cassette sensor 75 alone, both inflow and outflow cassette sensors 75 and 76, or from a separate pressure sensing tube 45 attached to sensor port 47.

As shown in FIG. 3, tubing set 14 may be set up as a "one-connection" arthroscopic tubing set or as a "two-connection" arthroscopic tubing set. (In a "two-connection" set-up, optional tube 45 and pressure port 39b would be utilized, but in a "one-connection" set-up they would not be utilized). The term "one-connection" refers to the number of irrigating fluid and pressure sensing connections at the work site. A one-connection tubing set utilizes one fluid inflow line such as tube 38 to supply fluid to a work site during a surgical procedure and provides pressure information to the pump flow control system within the console via a pressure transducer attached to the fluid inflow line and operative with sensor 75 to produce a pressure value. In this case, the pressure transducer is on the back of cassette housing 36 and sensor 75 is on front panel 15 adjacent cassette 36. Sensor 75 senses pressure in fluid tube 38 as described in the aforementioned U.S. Pat. No. 7,273,359. As will be understood by those skilled in the art, in arthroscopic procedures, one-connection systems are used with a simplified inflow cannula or scope sheath which does not have a separate pressure sensing port. Alternatively, an optional "two-connection" tubing set could also be used. In this case, scope sheath 39 is provided with a fluid inflow port 39a and a separate pressure sensing port 39b. The pressure sensing port 39b is connected via optional pressure sensing tube 45 to a pressure sensor/transducer 47 on pump console 12. A two-connection tubing set provides a way to determine pressure at the work site while a one-connection tubing set determines pressure at a given point in the fluid path. The pressure at the work site is herein referred to as True Intra-articular Pressure ("TIPS").

Since use of the TIPS system is optional, pump system 10 includes a method for determining the source of pressure information used to adjust the fluid flow and pressure produced by the system. Upon start-up, pump system 10 goes through a pressure determination sequence to identify the source of pressure data Pump system 10 first determines whether inflow pump 30 is operating (running) or not (stopped). In either case, the sequence of events regarding identifying the source of pressure data is the same. If the pressure sensed by the inflow cassette sensor 75 is greater than a predetermined amount, chosen in the preferred embodiment to be 25 mm Hg, the control system will check to see if sensor 47 is producing a signal, thus indicating the optional TIPS line 45 is being used. If the pressure is under the 25 mm Hg threshold, the system will default to operating in the "10K" mode, i.e. with measured pressure data coming from sensor 75. If the measured pressure data exceeds the threshold and a TIPS signal is detected, it is assured that the pump flow control system will continue to use this TIPS pressure data to control the operation of pump console 12. If no TIPS pressure signal is detected, it is determined whether to use pressure data from the inflow cassette sensor 75 only (the 10K mode) or from an alternate known as the Inferred Pressure Sensing ("IPS") mode. The IPS system will only be used as a source of pressure data if: (1) there is no TIPS signal at port 47, (2) there is pressure data at both inflow cassette sensor 75 and outflow cassette sensor 76, and (3) there is a difference between the pressures sensed by the inflow and outflow cassette sensors 75 and 76.

The pressure values used by the pump flow control system are monitored such that if the TIPS or IPS pressure data fails or if the TIPS and IPS pressure values are significantly different (e.g. by an order of magnitude) the system will revert to the 10K mode for pressure information. The pump flow control system is a servo control loop using, as inputs to a proportional integral derivative (PID) comparator, a set point equal to the pressure selected by a user on control panel 15 and a feedback signal equal to the actual pressure measured by the system (i.e. from the 10K mode. TIPS or IPS).

The Inferred Pressure Sensing ("IPS") system is used to indirectly calculate pressure at the surgical site without measuring pressure directly as is done by the TIPS tubing. The IPS system produces a pressure value based on sensed pressure and calculated flow at certain points in the tubing set and calculating the effect of pressure drops associated with certain components of the set. The sensed and calculated/inferred values are used in various equations to arrive at a calculated value representative of the pressure at the surgical site without having to actually measure pressure at the site. The advantage of this is that it enables the system to provide increased pressure measurement accuracy even with a wide variety of cannulas of different sizes. The IPS system is a method of accounting for fluid flow drops and pressure losses and compensating for these drops and losses to thereby maintain a more accurate pressure at the surgical site. The mathematical equation describing fluid flow and pressure drops through the various tubes of tubing set 14 is a complex polynomial described in detail in U.S. Pat. No. 7,510,542.

Pump system 10 also incorporates a declogging method for facilitating automatic removal of a blockage of the shaver aspirating tubing line 72. The declogging system comprises software driven steps which control the output pump 40 to activate this function. The declogging feature operates during use of handpiece 70 by sensing various characteristics of the operation of system 10 to determine the likelihood of a clog. If the outflow peristaltic rotor is working and the inflow peristaltic rotor is not working (or if the inflow rotor speed is significantly less than the outflow rotor speed) and if pressure at the work site (or pressure at both cassettes) is not changing, it is probable that the shaver blade or aspiration line 72 is clogged. In this event, the user may activate a declog button (not shown) which causes the outflow rotor to be activated in the opposite direction for a time period sufficient to create a pressure pulse to move approximately 5-15 ml of fluid through outflow line 72, handpiece 70 and shaver 73. After this time period, the outflow rotor resumes normal operation. In the preferred embodiment, 5-15 ml of fluid displacement is deemed sufficient for the size of the tubing used. Approximately 5 ml of fluid (approximately 6.2 inches (157.48 mm) long in a 0.25 inch (6.35 mm) internal diameter tube) is an estimate of a volume sufficient to move the fluid back to the clog, and another approximately 5 ml is an estimate of the fluid required to push the clog out. In use, the surgeon would remove the shaver from the work site and aim it at a waste container. The declog button would cause the outflow rotor to be run in reverse as quickly as possible for approximately three revolutions and then forward for approximately six revolutions to push the clog out.

Figure 4:
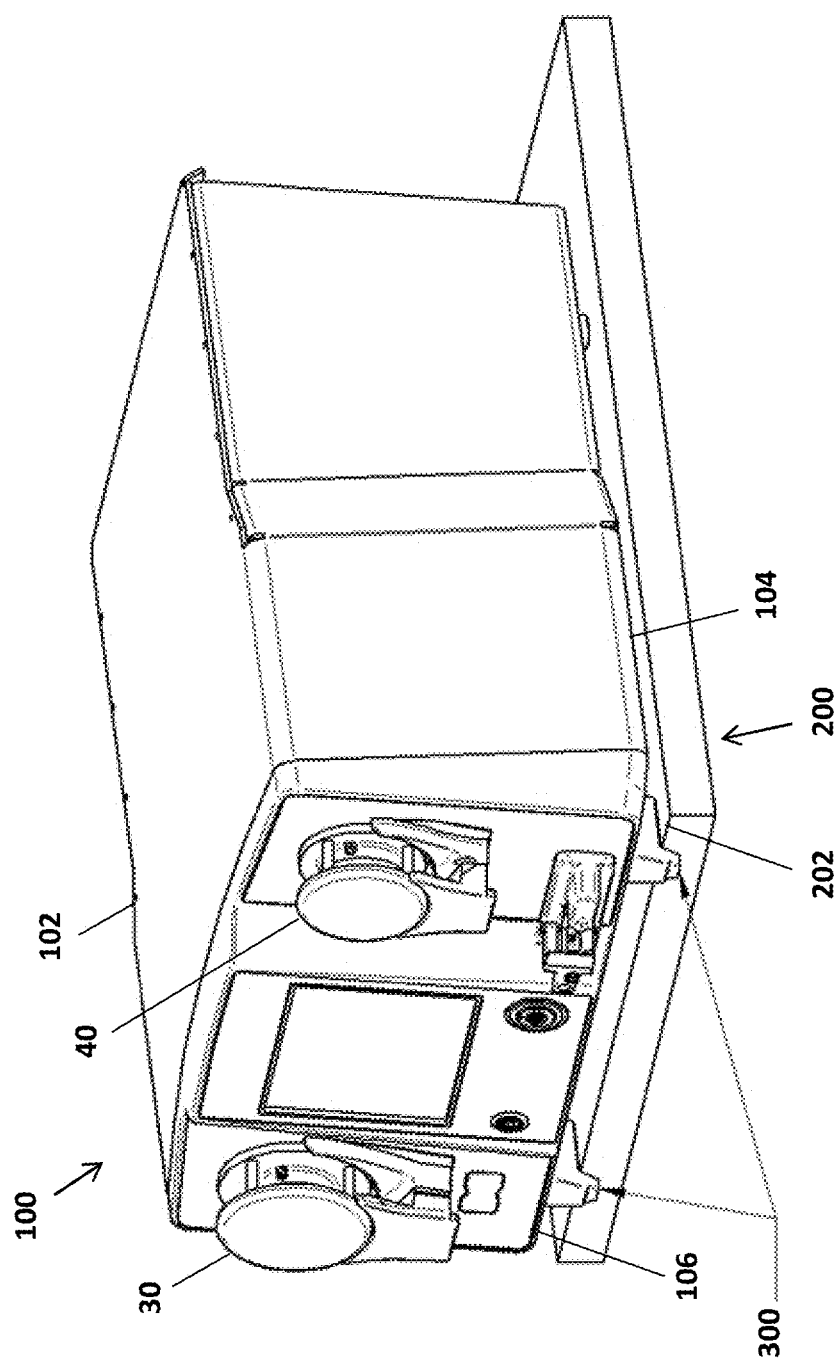
FIG. 4 is a perspective view schematic representation of a pump system, according to an alternative embodiment.

Turning now to FIG. 4, there is shown a perspective view schematic representation of a pump system 100, according to an alternative embodiment. As shown in FIG. 4, the pump system 100 comprises a console 102, similar to that described above with reference to FIGS. 1-3. In the embodiment depicted in FIG. 4, the console 102 is positioned or otherwise located on a surface 200. The surface 200 is preferably a flat surface. The surface 200 can be any surface where the pump system 100 is placed thereon for use in surgical procedures or even storage. For example, the surface 200 can be a surface on a shelf or cart.

As recited above, traditional pump systems slide along the surface and/or cause kinking in the tubing sets due to movement of the console along the surface. The console 102 in FIG. 4 provides one or more anti-sliding features 300 that prevent to undesirable movement of the console 102 along the surface 200. In the depicted embodiment, the anti-sliding feature 300 is a "shelf stop foot" (also referred to herein as a "foot"). As shown in FIG. 4, there are two feet 300 extending at least partially between a bottom side 104 of the console 102 and the surface 200. In the embodiment shown in FIG. 4, the feet 300 extend below a front edge 106 of the console 102. Further, as also shown in FIG. 4, at least a portion of each foot 300 extends over a front edge 202 of the surface 200.

Figure 5:
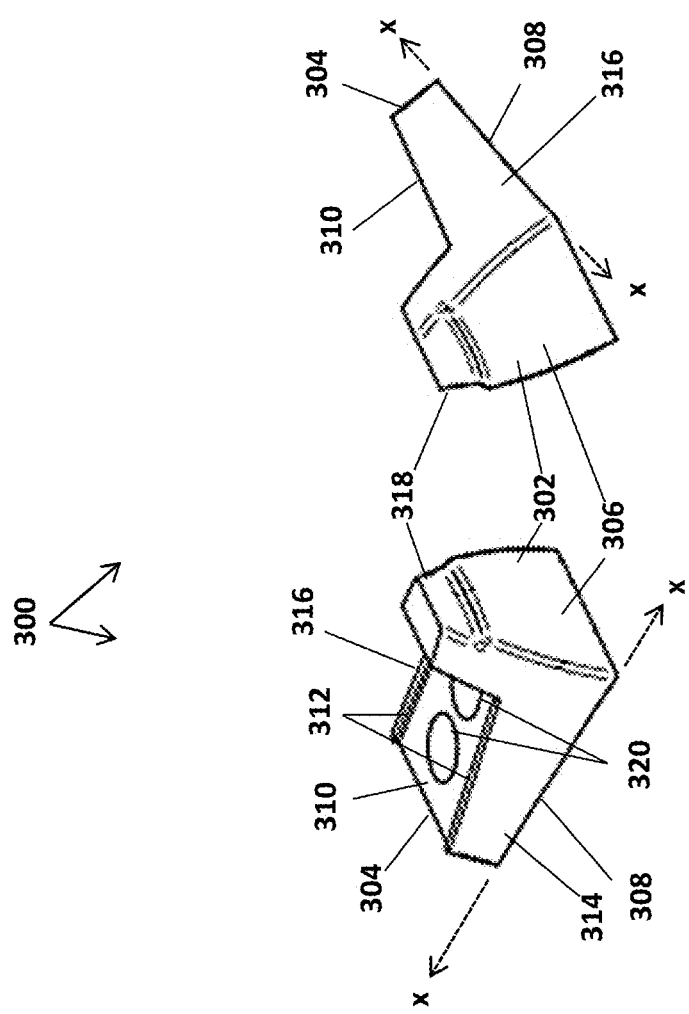
FIG. 5 is a perspective view schematic representation of a foot, according to an embodiment.

Referring now to FIGS. 5-9, there are shown various views schematic representations of the shelf stop foot 300, according to an embodiment. FIG. 5 shows a perspective view schematic representation of the foot 300. The foot 300 is a sloped body 302 having a first end 304 and a second end 306. In the depicted embodiment, the foot 300 has a first surface 308 and a second surface 310. In the depicted embodiment, the first surface 308 is a flat surface extending along a first plane x-x between the first end 304 and the second end 306.

Figure 6:
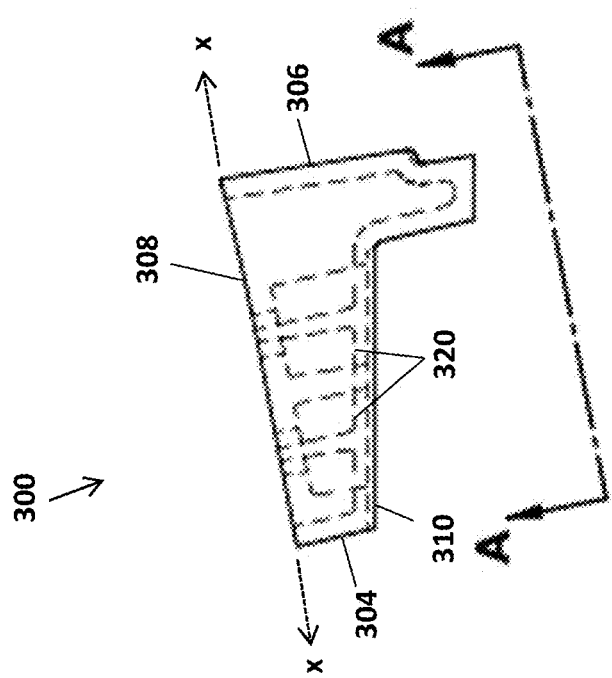
FIG. 6 is a side view schematic representation of the foot, according to an embodiment.

The second surface 310 extends between the first end 304 and the second end 306 at an angle relative to the first plane x-x, as shown in the side view schematic representation of the foot 300 in FIG. 6. Referring back to FIG. 5, the second surface 310 comprises a pair of opposing, raised edges 312. The raised edges 312 extend from a first side 314 of the body 302 and a second side 316 of the body 302. The raised edges 312 extend along the second surface 310 and up to a protrusion 318 extending from the second end 306 of the body 302. In the depicted embodiment, the protrusion 318 is rectangular, forming an L-shaped body 302.

Figure 7:
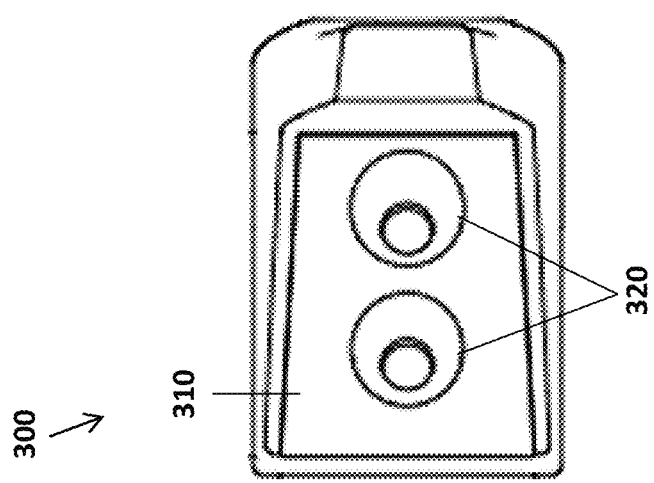
FIG. 7 is a top perspective view schematic representation of the foot, according to an embodiment.

As shown in FIG. 5, the body 302 includes one or more apertures 320 extending therethrough from first surface 308 to the second surface 310. In the embodiment shown in FIG. 5, the body 302 comprises two apertures 320 extending through the first surface 308 to the second surface 310. FIG. 7 shows a top perspective view schematic representation of the foot 300, according to an embodiment. As shown in FIGS. 6 and 7, the diameter of the apertures 320 vary between the first surface 308 and the second surface 310.

Figure 8:
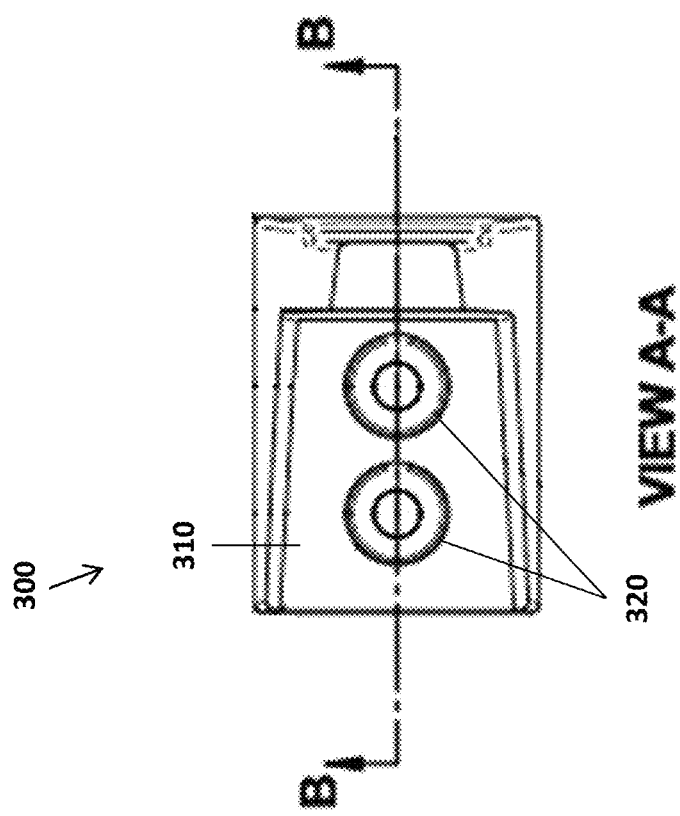
FIG. 8 is a top sectional view schematic representation of the foot, according to an embodiment.
Figure 9:
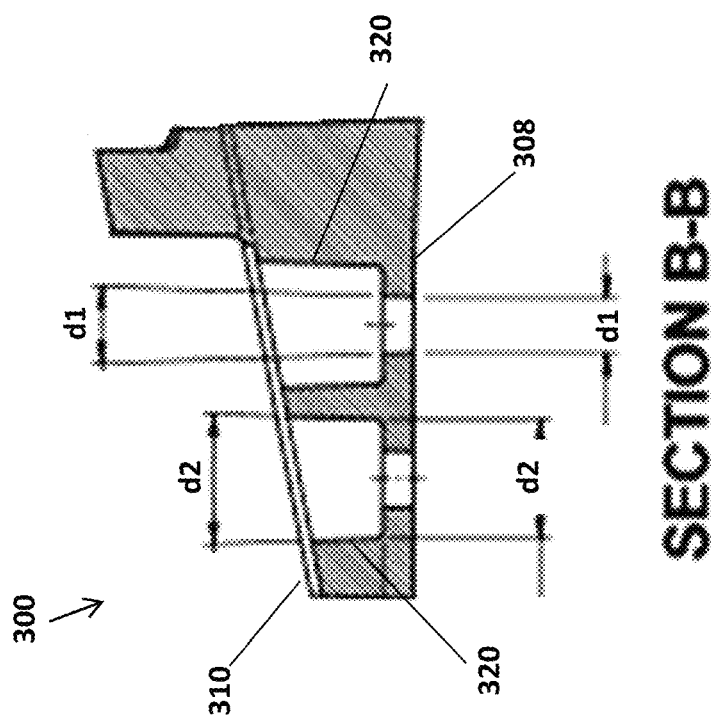
FIG. 9 is a side sectional view schematic representation of the foot, according to an embodiment.

Specifically, FIGS. 8 and 9 show a top and side sectional views schematic representations of the foot 300, according to an embodiment. As shown, the apertures 320 have a first diameter d1 at the first surface 308 of the foot 300 and a second diameter d2 at the second surface 310 of the foot 300. The varying diameters d1, d2 of the apertures 320 accommodates a connector (not shown), such as a screw or a pin, for example. The change in diameter within the apertures 320 may be abrupt, such as that shown in FIG. 9, or the apertures 320 may be tapered such that the diameter decreases from the first surface 308 to the second surface 310. The change in diameter within each aperture 320 depends on the type of connector used. Any known connectors can be used within the aperture 320.

Figure 10:
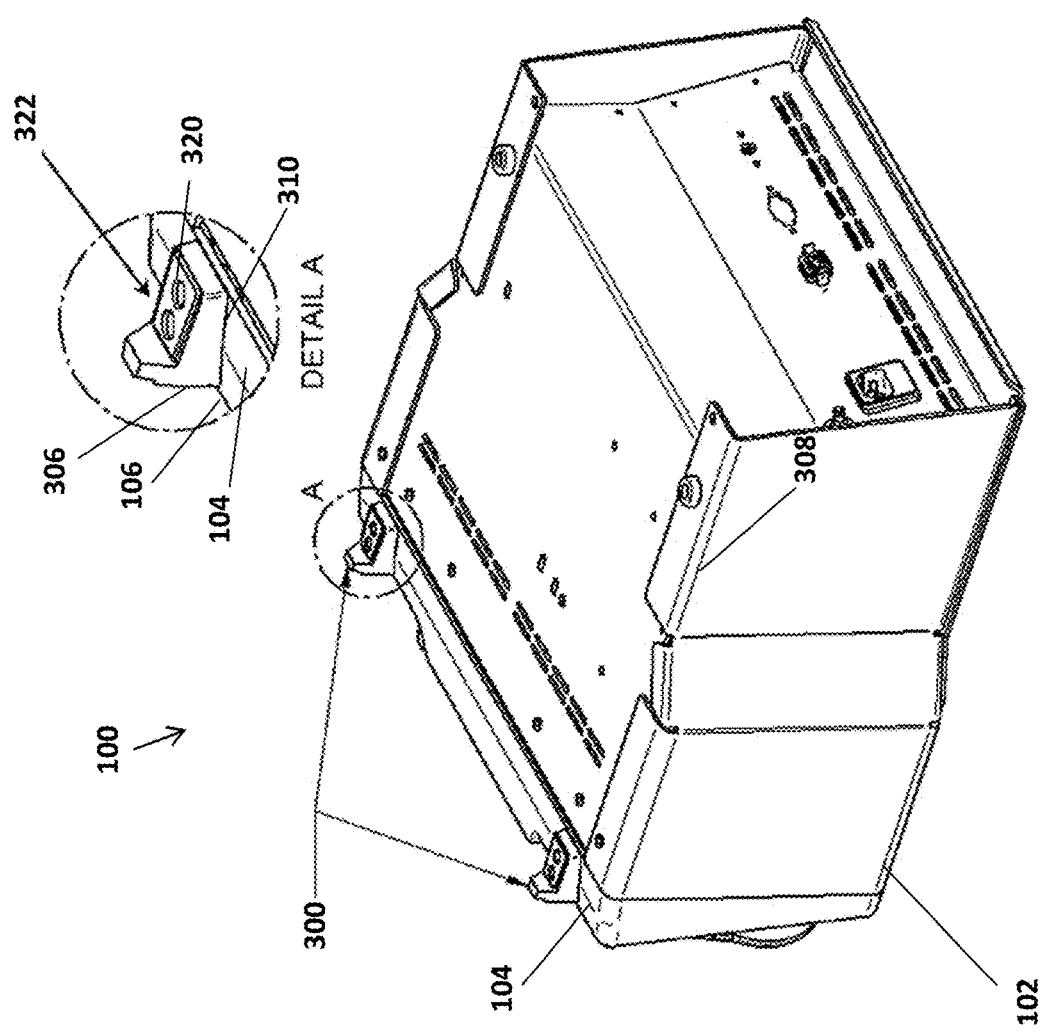
FIG. 10 is a perspective view schematic representation of the bottom side of the console, according to an embodiment.

Referring now to FIG. 10, there is shown a perspective view schematic representation of the bottom side 104 of the console 102, according to an embodiment. FIG. 10 shows how the feet 300 are attached to the bottom side 104 of the console 102. Any number of feet 300 can be attached to the bottom side 104 of the console 102. Generally, a larger console 102 requires additional feet 300. In the depicted embodiment, two feet 300 are attached to the bottom side 104 of the console 102.

To attach each foot 300 to the console 102, the second surface 310 of the console 102 is positioned against the bottom side 104 of the console 102. The angled second surface 310 is configured to extend along and complimentary to an angled bottom side 104 of the console 102. Each foot 300 is positioned such that the second end 306 of the foot 300 outward, away from the console 102. Specifically, as shown in FIG. 10, the second end 306 of the foot 300 is substantially aligned with a front edge 106 of the console 102.

Still referring to FIG. 10, each foot 300 comprises an anti-sliding or anti-slip material. As shown in FIG. 10, a sheet 322 of non-stick material is attached to the second surface 310 of the foot 300. As shown in FIG. 10, the sheet 322 of material extends along the second surface 310 around each aperture 320. In an embodiment, the sheet 322 is composed of Bumpon® material felastomeric protector material having an adhesive on one side for attachment to various surfaces to provide protection thereto) having one or more apertures 320 extending therethrough. Other similar anti-sliding material, such as a rubber-based material can be used. The apertures 320 in the sheet 322 align with the apertures 320 in the foot 300 as to not create interference between any connectors (not shown) and the sheet 322. The sheet 322 may have a self-adhesive side, making it attachable to the second surface of the foot 300. However, any other attachment means may be used.

With the feet 300 attached to the bottom side 104 of the console 102, the console 102 is placed onto the surface 200, as shown in FIG. 4. The console 102 is positioned such that the protrusion 318 of each foot 300 extends over the front edge 202 of the surface 200. With the protrusions 318 essentially hooked around the surface 200, the console 102 resists sliding in the opposing direction away from the front edge 202 of the surface 200. Additionally, the console 102 is positioned such that the second surface 310 rests on the surface 200. In the embodiment of the console 102 shown in FIG. 4, the sheet 322 of ant-sliding material rests on the surface 200, providing additional anti-sliding properties.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An irrigation system, comprising:
a console having a front panel with an inflow pump and an outflow pump, the front panel extending to a front edge and the front edge connected to a bottom side of the console;
one or more feet attached to the bottom side of the console, each foot comprising:
a first planar surface extending in a first plane from a first end to a second end, wherein the first plane faces the console;
a second planar surface opposite the first surface, extending in a second plane at an angle to the first plane from the first end to a third planar surface proximate to the second end, wherein the third surface extends in a third plane at an angle to the first and second planes and in a direction away from the first surface, the second surface and the console, and wherein the third surface extends to and ends at a fourth planar surface extending in a fourth plane extending at an angle to the third plane, wherein the fourth surface is the furthest surface away from and opposite to the first surface, wherein the fourth surface faces away from the first planar surface, wherein the first surface and the second surface are directly connected by a fifth planar surface, wherein the first surface is directly connected to and extends from the fifth planar surface to a sixth planar surface, and wherein the sixth planar surface is opposite to the fifth planar surface and is directly connected to and extends from the first surface toward the fourth surface.

2. The system of claim 1, wherein at least a portion of the one or more feet extend from the front edge of the front panel of the console.

3. The system of claim 1, further comprising one or more apertures extending through the first surface and the second surface of the one or more feet.

4. The system of claim 3, wherein each aperture has a first diameter and a second diameter, the second diameter different from the first diameter.

5. The system of claim 3, wherein each of the one or more apertures are adapted to receive a connector.

6. The system of claim 1, wherein the one or more feet are adapted to rest on a surface such that the protrusion extends over a front edge of the surface.

7. The system of claim 1, further comprising a sheet of rubber material extending across the second surface.

8. The system of claim 7, wherein the sheet of rubber material has one or more apertures aligned with one or more apertures extending through the first surface and the second surface of the one or more feet.

\* \* \* \* \*